United States Patent
Harada et al.

(10) Patent No.: US 7,884,614 B2
(45) Date of Patent: Feb. 8, 2011

(54) DEVICE OF ELECTRODES FOR MEASURING WATER CONTENT IN FOUNDRY SAND, AN APPARATUS FOR MEASURING WATER CONTENT IN FOUNDRY SAND, AND A METHOD AND AN APPARATUS FOR SUPPLYING WATER TO A SAND MIXER

(75) Inventors: Hisashi Harada, Toyokawa (JP); Tadashi Nishida, Toyokawa (JP); Kozo Sugita, Toyokawa (JP)

(73) Assignee: Sintokogio, Ltd., Aichi-ken (JP)

( * ) Notice: Subject to any disclaimer, the term of this patent is extended or adjusted under 35 U.S.C. 154(b) by 1032 days.

(21) Appl. No.: 11/631,601

(22) PCT Filed: Jul. 6, 2005

(86) PCT No.: PCT/JP2005/012462

§ 371 (c)(1),
(2), (4) Date: Jan. 5, 2007

(87) PCT Pub. No.: WO2006/004147

PCT Pub. Date: Jan. 12, 2006

(65) Prior Publication Data

US 2008/0056060 A1    Mar. 6, 2008

(30) Foreign Application Priority Data

Jul. 7, 2004    (JP) ............................... 2004-200636

(51) Int. Cl.
*G01N 27/02* (2006.01)
*G01R 27/08* (2006.01)

(52) U.S. Cl. ...................... 324/448; 324/441; 324/444; 324/449; 324/694; 324/702; 324/724

(58) Field of Classification Search ................. 324/439, 324/441, 444, 446, 448, 449, 694, 702, 703, 324/724

See application file for complete search history.

(56) References Cited

U.S. PATENT DOCUMENTS

| | | | | |
|---|---|---|---|---|
| 2,838,730 A | * | 6/1958 | Lebourg | 324/324 |
| 3,808,881 A | * | 5/1974 | Dietert | 73/794 |
| 4,088,945 A | * | 5/1978 | Howell et al. | 324/351 |
| 4,141,404 A | * | 2/1979 | McMullen | 164/456 |
| 4,569,025 A | * | 2/1986 | Eirich et al. | 700/265 |
| 4,652,811 A | * | 3/1987 | Kwiat et al. | 324/694 |
| 4,780,665 A | * | 10/1988 | Mitchell | 324/695 |
| 5,302,781 A | * | 4/1994 | Hanson, III | 324/367 |
| 5,497,091 A | * | 3/1996 | Bratton et al. | 324/449 |
| 6,377,052 B1 | * | 4/2002 | McGinnis et al. | 324/446 |

FOREIGN PATENT DOCUMENTS

| | | |
|---|---|---|
| JP | 56-141547 A | 11/1981 |
| JP | 5052798 | 3/1993 |
| WO | WO2004003534 | 1/2004 |

\* cited by examiner

*Primary Examiner* — Timothy J Dole
(74) *Attorney, Agent, or Firm* — Finnegan, Henderson, Farabow, Garrett & Dunner, L.L.P.

(57) ABSTRACT

This invention relates to a device of electrodes for measuring water content in foundry sand, an apparatus for measuring water content in foundry sand, and a method and an apparatus for supplying water to a sand mixer. When the prior art device for measuring water content in the foundry sand is disposed in it, the size or shape of the device of the electrodes is limited. To solve this problem, the device of the electrodes for measuring water content in the foundry sand by supplying an electric current to it is comprised of a plurality of conductive elements 2, 3 concentrically disposed with certain intervals between them in a longitudinal direction, wherein the elements form an annular shape, a retaining element 4 to retain the plurality of the conductive elements 2, 3, wherein the retaining element 4 has an electrical insulating property and a cylindrical shape having the same diameter as the conductive elements 2, 3, and the two conductive wires 5, 6 to connect alternate respective elements of the plurality of conductive elements 2, 3 so that the conductive elements 2, 3 form two poles, wherein the two conductive wires 5, 6 pass through the cavity in the retaining element 4.

6 Claims, 4 Drawing Sheets

DEVICE OF ELECTRODES FOR MEASURING WATER CONTENT IN FOUNDRY SAND, AN APPARATUS FOR MEASURING WATER CONTENT IN FOUNDRY SAND, AND A METHOD AND AN APPARATUS FOR SUPPLYING WATER TO A SAND MIXER

TECHNICAL FIELD

This invention relates to a device of electrodes for measuring water content in foundry sand, an apparatus for measuring water content in foundry sand, and a method and an apparatus for supplying water to a sand mixer.

BACKGROUND OF THE INVENTION

A conventional apparatus for measuring water content in foundry sand by applying an electric current to the foundry sand uses a device of electrodes to supply the electric current to it. The device of the electrodes is comprised of a plurality of elements of electrodes disposed parallel to each other with certain intervals between them, wherein the elements form a square bar and have electrical conductivity, a retaining element to retain the plurality of the elements of the electrodes so that the upper surfaces of the elements of the electrodes are exposed, wherein the retaining element has an electrical insulating property, and connecting means to alternately connect the plurality of the elements of the electrodes to each other so that the connected elements of electrodes form two poles, wherein the means have electrical conductivity.

However, for the conventional device for measuring the water content in foundry sand having the above constitution, when it is disposed in a hopper storing the foundry sand, a rather large space is required in the hopper.

Here, "water content in foundry sand" is defined as an amount of water contained in it and expressed as a percentage of the weight of the water in the foundry sand of a unit weight. It is possible to control the properties of return foundry sand so that it has the optimum properties as foundry sand used for molding a mold by measuring the water content in the foundry sand.

Patent document 1: WO 2004/003534 A1

DISCLOSURE OF INVENTION

The problem to be solved is that there is a limitation in the size or the shape of the device of the electrodes, when the device for measuring the water content in the foundry sand is disposed in the foundry sand.

To solve this problem, the invention relates to a device of electrodes for measuring water content in foundry sand, is provided with the following constitution. Namely, the device of the electrodes for measuring the water content in the foundry sand by supplying an electric current to it comprises a plurality of conductive elements concentrically disposed with certain intervals between them in a longitudinal direction, wherein the elements form an annular shape, a retaining element to retain the plurality of the conductive elements, wherein the retaining element has an electrical insulating property and a cylindrical shape having the same diameter as the conductive elements, and two conductive wires to connect alternate respective elements of conductive elements so that the conductive elements form two poles, wherein the two conductive wires pass through the cavity in the retaining element.

According to this invention, since the device of the electrodes has a bar-like shape, and since the two conductive wires pass through the interior portion of it, it can be downsized and become compact. Thus, no large space is required to place the device of the electrodes for measuring water content in the foundry sand.

As explained in the above paragraphs, the device of the electrodes for measuring water content in foundry sand by supplying an electric current to it, comprises a plurality of conductive elements concentrically disposed with certain intervals between them in a longitudinal direction, wherein the elements form an annular shape, a retaining element has an electrical insulating property and a cylindrical shape having the same diameter as the conductive elements, and two conductive wires to connect alternate respective elements of the plurality of conductive elements so that the conductive elements form two poles, wherein the two conductive wires pass through the cavity in the retaining element.

Thus, the invention has a beneficial effect in that the device of the electrodes can be used without a limitation in the size or shape of the space in the foundry sand in which to place it.

PREFERRED EMBODIMENTS OF THE INVENTION

Figure 1:
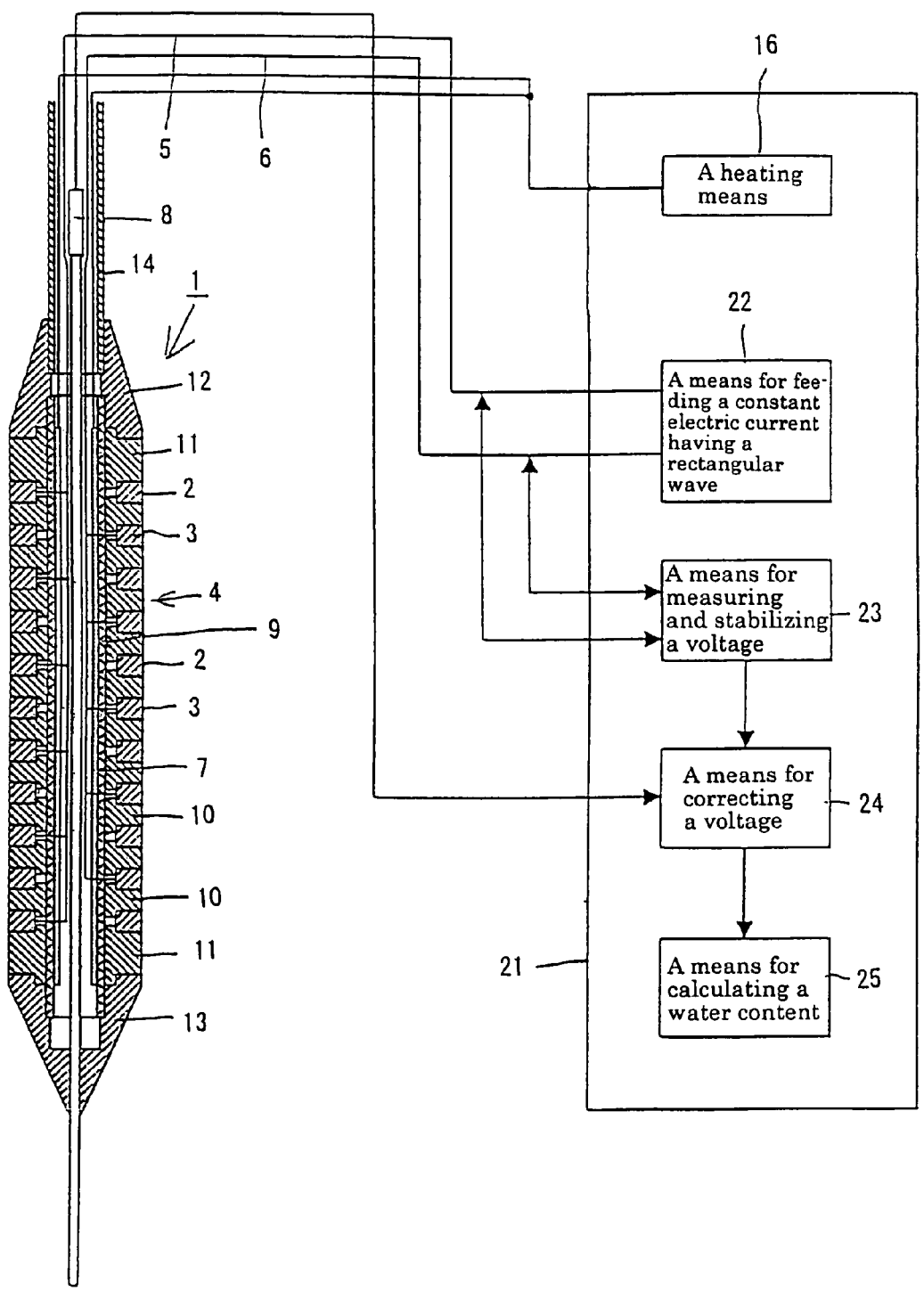
FIG. 1 shows a vertical cross-sectional view of the device of the electrodes and a diagram of the apparatus for controlling it, of a preferred embodiment of this invention.

A preferred embodiment of this invention for a device of electrodes for measuring water content in foundry sand is now explained in detail based on the figures. As shown in FIG. 1, the device of the electrodes 1 of this invention for measuring the water content in foundry sand is comprised of the following: a plurality of conductive elements 2•2, 3•3 concentrically disposed with certain intervals between them in a longitudinal direction, wherein the elements form an annular shape; a retaining element 4 to retain the plurality of the conductive elements 2•2, 3•3, wherein the retaining element 4 has an electrical insulating property and a cylindrical shape having the same diameter as that of the conductive elements 2•2, 3•3; two conductive wires 5•6 to connect alternate respective elements of the plurality of conductive elements 2•2, 3•3 so that they form two poles, wherein the two conductive wires 5•6 pass through the cavity in the retaining element 4; an electric heater 7 disposed in the retaining element 4 having the electrical insulating property; and a thermocouple 8 as a means for measuring temperature, wherein the thermocouple 8 passes through the retaining element 4 and is disposed in it.

The conductive elements 2•2, 3•3 are made of a metal material having excellent resistance to corrosion. The retaining element 4 is comprised of: a core portion 9 having a cylindrical shape, a plurality of short ring parts 10•10 disposed at the outer side of the core portion 9, long ring parts 11•11 disposed at the upper and the lower end of the short ring parts 10•10 and at the outer side of the core portion 9, which long ring parts 11•11 are a little longer than the short ring parts 10•10, upper and lower holding parts 12•13 to hold the short ring parts 10•10 and the long ring parts 11•11 by screwing the upper and the lower end of the core portion 9 into the upper and the lower holding parts 12•13 respectively, which holding parts 12•13 have a hollow and conical shape. The short ring parts 10•10, the long ring parts 11•11, and the upper and the lower holding parts 12•13 are made of super-high-molecular polyethylene or alumina ceramics, by, for example, machining, molding, or heat-treatment after molding.

The electric heater 7 is connected to a heating means 16 and has a tape-like shape. The thermocouple 8 is attached at a supporting member 14, which is disposed at the upper portion of the upper holding parts 12, and extends downward 50 mm below the lower portion of the retaining element 4 having an electrical insulating property. As explained above, since the distal end of the thermocouple 8 extends downward more than 30 mm below the lower portion of the retaining element 4, it is not affected by the heat generated by the electric heater 7. The two conductive wires 5•6 connect alternate respective elements of the plurality of the conductive elements 2•2, 3•3 so that the conductive elements 2•2, 3•3 form the two poles. As an alternative solution, the leading ends of the two wires 5•6 can be connected to the upper conductive elements 2, 3, and alternate respective elements of the plurality of the conductive elements 2•2, 3•3 can be connected to each other by connecting means, such as a screw, made of the same material as that of the conductive elements 2•2, 3•3, so that the conductive elements 2•2, 3•3 form the two poles.

Considering that the device of the electrodes 1 is installed in an existing hopper, and that it has to measure the water content of the foundry sand in the hopper, the dimensions of it are determined as follows. The conductive elements 2, 3 have a diameter of 30-100 mm and a length of 5-20 mm. The short ring parts 10 of the retaining element 4 have a height of 5-20 mm, in order to keep the intervals between the conductive elements 2, 3 at predetermined values and to retain their electrical insulating property.

Since the device of the electrodes 1 has such a constitution as is explained above, it has a cylindrical column-like configuration as a whole, and the two wires 5•6 can pass through the device of the electrodes 1. Thus, since the device of the electrodes 1 becomes compact, the space for placing it in foundry sand becomes rather smaller. Dew condensation on the surfaces of the conductive elements 2•2, 3•3 can be prevented by heating them with the electric heater 7 by activating the heating means 16. For the conventional device of the electrodes, a thermocouple is installed so that it is separated from the device. However, for the present invention, since the thermocouple 8 is integrated with the device of the electrodes 1 by disposing it in the cavity of the retaining element 4, a device which has a compact shape can be achieved.

Next, a controlling device 21 to control the device of the electrodes 1 for measuring water content in foundry sand is explained based on FIG. 1. As shown in FIG. 1, the device of the electrodes 1 is electrically connected to the controlling device 21. The controlling device 21 is comprised of: a means 22 for supplying a constant electric current having a rectangular wave and a low frequency to the conductive elements 2•3 of the device of the electrodes 1 through the two conductive wires 5•6, a means 23 for measuring and stabilizing the voltage generated between the two conductive wires 5•6 by the electric current between the conductive elements 2•2, 3•3 through the foundry sand, a means 24 for correcting the voltage measured and filtered by the means 23 based on the measured temperature of the foundry sand, and a means 25 for calculating the water content in the foundry sand based on the filtered voltage corrected by the means 24.

After the device of the electrodes 1 is placed in the foundry sand to be measured, the electric current is caused to flow between the conductive elements 2•2, 3•3 through the foundry sand by supplying a constant electric current having a rectangular wave and a low frequency to the conductive elements 2•2, 3•3 of the device of the electrodes 1 by means of the means 22 of the controlling device 21. Then, the voltage generated between the two conductive wires 5•6 is measured and filtered by the means 23 for measuring and stabilizing it. Further, the voltage filtered by the means 23 is corrected by the means 24 of the controlling device 21 based on the temperature measured by using the signal from the thermocouple 8. Then the water content in the foundry sand is calculated by the means 25 of the controlling device 21 based on the filtered and corrected voltage. The calculated water content, for example, is illustrated in FIG. 2.

Figure 2:
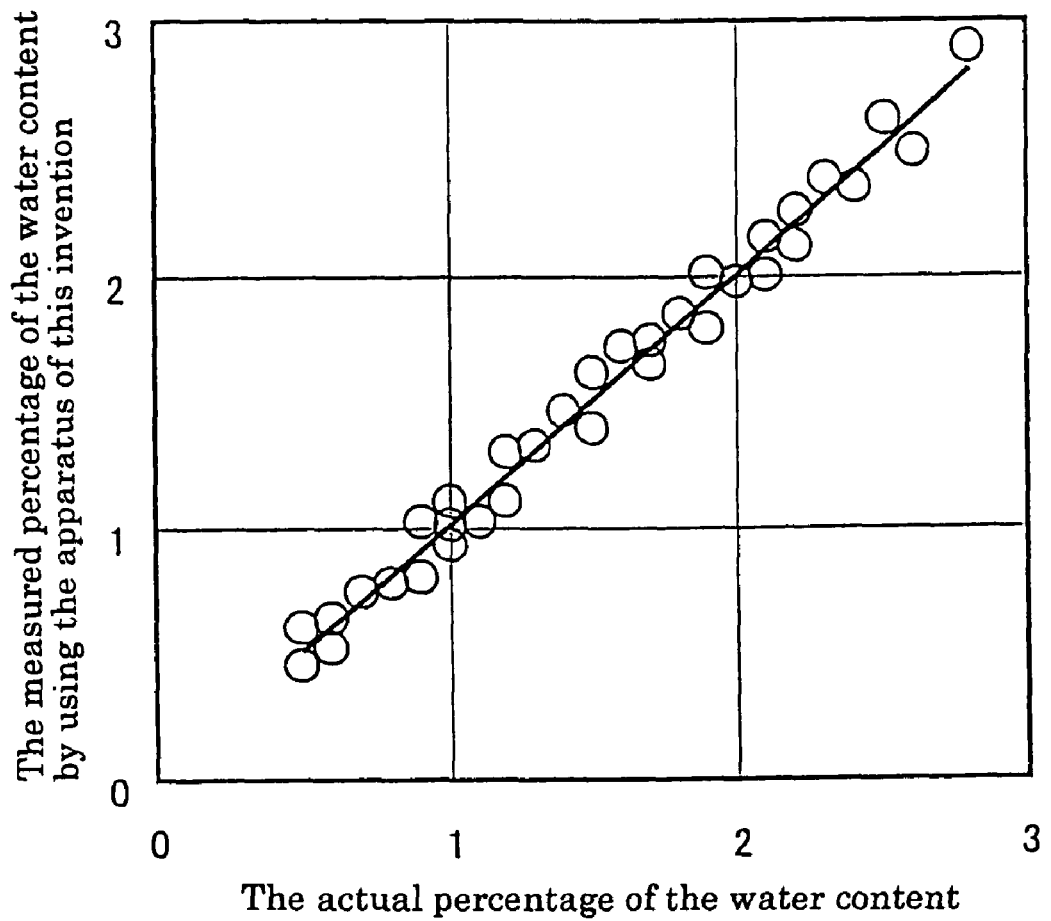
FIG. 2 shows a sample of measurements of the water content in foundry sand by using the apparatus for measuring it of this invention.

FIG. 2 shows the results of measurements of the water content of foundry greensand returned after disassembling the flasks. The horizontal scale of the chart of FIG. 2 shows the water content (the actual content of the percent of the water) obtained by measuring the water content that has evaporated from the foundry greensand by heating it. The vertical scale of it shows the water content (the measured content of the percent of the water) measured by the controlling device 21 of this invention. The chart of FIG. 2 shows that the water content measured by the device of this invention corresponds to the actual content of the water within the range of 0.5%-3% of the actual water content of the foundry greensand.

Figure 3:
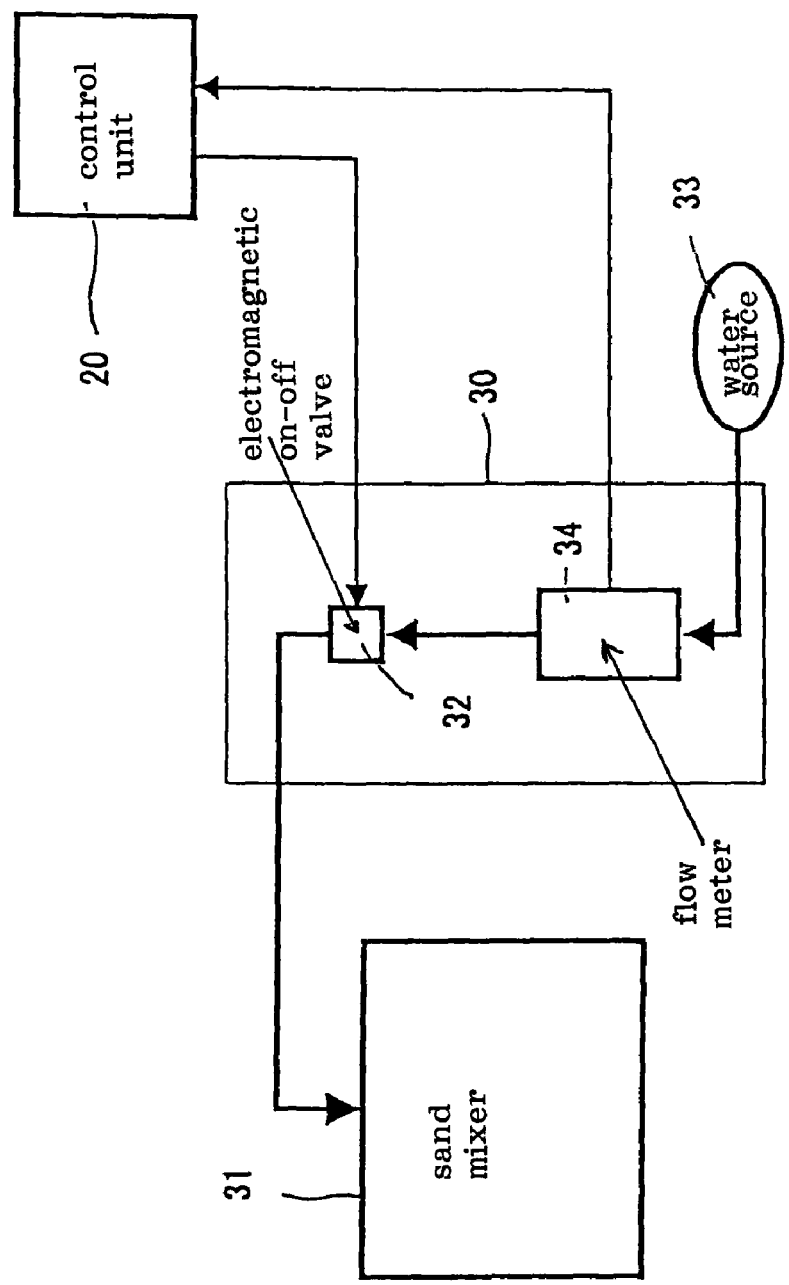
FIG. 3 shows a block diagram of one embodiment of a sand mixer using the device with a controlling device for measuring water content in foundry sand and an apparatus for supplying water to the mixer of this invention.

Next, a method for supplying necessary water to foundry sand in a sand mixer 31 is explained based on FIG. 3. The water is supplied to the sand mixer 31 by controlling an apparatus for supplying water 30 having a hydraulic circuit that is constituted of a digital flow meter 34 communicating with a water source 33 and an electromagnetic on-off valve 32 serially connected to the flow meter 34 by the control unit 20, which is constituted by the device of the electrodes 1 and the controlling device 21. For the apparatus for supplying the water 30, the water is supplied to the sand mixer 31 by opening the electromagnetic on-off valve 32 of the apparatus 30 based on the signal from the control unit 20. The quantity of the water flowing through the electromagnetic on-off valve 32 is integrated by the digital flow meter 34. The timing for shutting down the electromagnetic on-off valve 32 is controlled by the signal transmitted from the controlling device 21 of the control unit 20 to the electromagnetic on-off valve 32, which signal is transmitted ahead of time so as to compensate for the amount of water flowing into the sand mixer 31 after the valve 32 is closed based on the measurement of that water.

Figure 4:
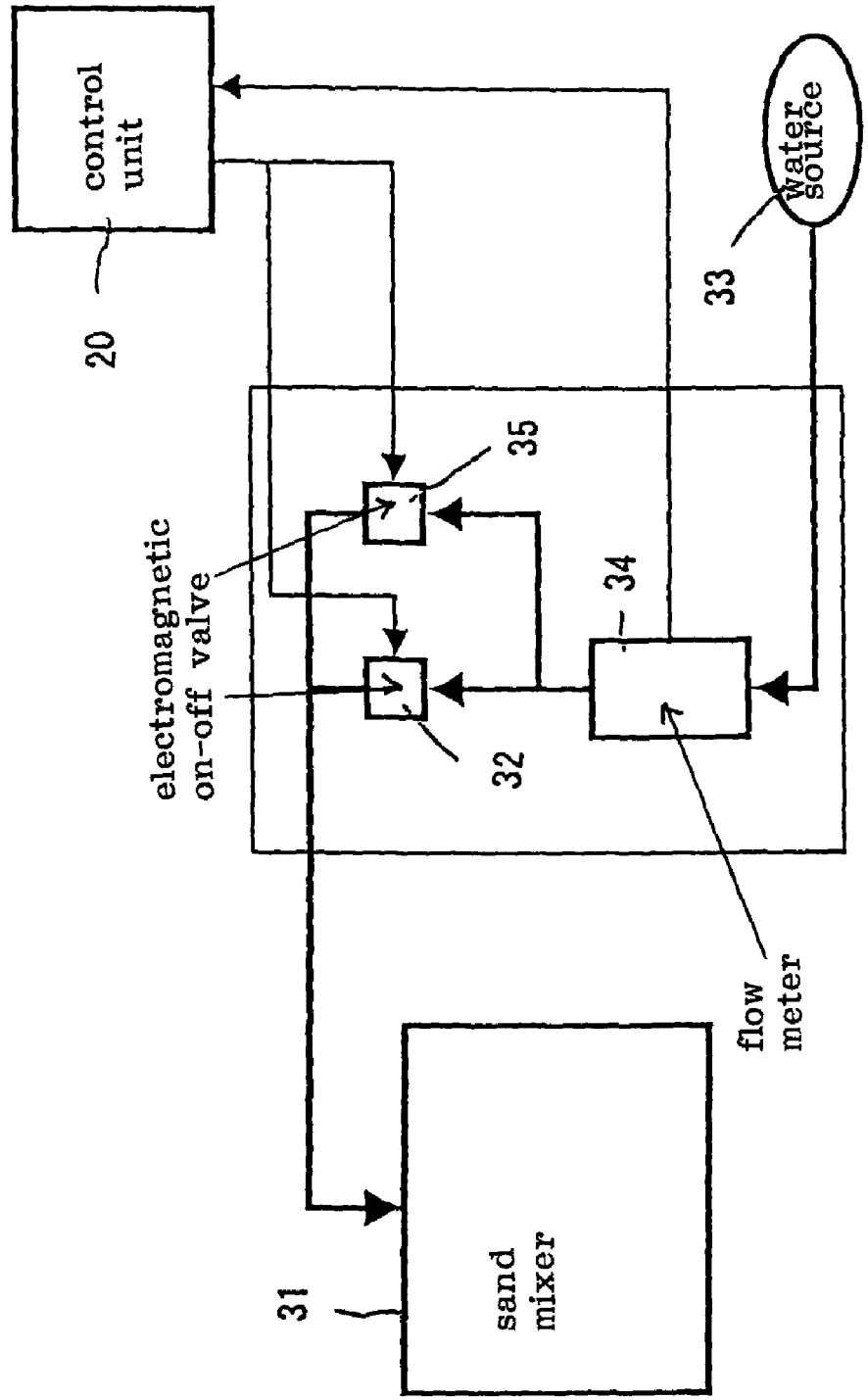
FIG. 4 shows a block diagram of another embodiment of a sand mixer using the device with a controlling device for measuring water content in foundry sand and an apparatus for supplying water to the mixer of this invention.

FIG. 4 shows another embodiment of the method for supplying necessary water to the sand mixer 31. In FIG. 4, another electromagnetic on-off valve 35 is connected in parallel to the electromagnetic on-off valve 32 of the hydraulic circuit. It is constituted of a digital flow meter 34 that communicates with a water source 33 and an electromagnetic on-off valve 32 serially connected to the flow meter, as shown in FIG. 3. The ratio of the flow rate of the two electromagnetic on-off valves 32 and 35 can be set between 1:2 and 1:10. When it begins to supply the water to the sand mixer 31, both of the electromagnetic on-off valves 32 and 35 are opened by the signal from the controlling device 21 of the control unit 20. Then the quantity of the water flowing through the valves is combined by the digital flow meter 34. When the quantity of the water fed to the sand mixer reaches the predetermined value, which is determined based on the necessary amount of water, the electromagnetic on-off valve 35 is closed, and the electromagnetic on-off valve 32 continues supplying the water to the sand mixer 31. Then the timing for closing the electromagnetic on-off valve 32 is controlled by the signal transmitted from the control unit 20 to it which signal is transmitted ahead of time so as to compensate for the amount of water flowing into the sand mixer 31, based on the measurement of the water flowing into the sand mixer 31 after the valve 32 is closed. In this way it completes supplying the water to the sand mixer 31. According to these methods explained here, even if the pressure of the water source 33 of the apparatus 30 changes, or even if the flow rate of the water in the hydraulic circuit is reduced, it is still possible to precisely supply the water to the sand mixer 31.

What we claim is:

1. An apparatus for measuring water content in foundry sand, comprising:
   a device of electrodes for measuring water content in foundry sand that includes:
   a plurality of conductive elements concentrically disposed in a longitudinal direction with certain intervals between them, wherein the conductive elements form an annular shape,
   a retaining element to retain the plurality of the conductive elements, wherein the retaining element has an electrical insulating property and a cylindrical shape having the same diameter as the conductive elements,
   two conductive wires to connect alternate respective elements of the plurality of conductive elements so that the conductive elements form two poles, wherein the two conductive wires pass through a cavity in the retaining element, and
   means for measuring temperature disposed in a cavity in the retaining element, wherein a distal end of the means for measuring temperature protrudes outside the retaining element,
   means for supplying a constant electric current having a rectangular wave and a low frequency to the conductive elements of the device of electrodes through the two conductive wires,
   means for measuring and stabilizing a voltage generated between the two conductive wires by an electrical current flowing between the conductive elements through the foundry sand,
   means for correcting the voltage measured and stabilized by the means for measuring and stabilizing the voltage based on the temperature of the foundry sand measured by the means for measuring temperature, and
   means for calculating the water content in the foundry sand based on the voltage corrected by the means for correcting the voltage.

2. The apparatus of claim 1, further comprising an electric heater disposed in a cavity in the retaining element.

3. The apparatus of claim 1, wherein the distal end of the means for measuring temperature protrudes more than 30 mm from a lower portion of the retaining element.

4. A method for supplying water to foundry sand in a sand mixer, comprising:
   a calculating step to determine a difference between a value of necessary water content in foundry sand after mixing the foundry sand and a value of water content in the foundry sand measured by the apparatus of claim 1 for measuring water content before mixing the foundry sand,
   a calculating step to determine a necessary quantity of the water to be supplied to the sand mixer,
   a step for starting to supply water to the sand mixer by opening an electromagnetic on-off valve for controlling a supply of water from a water source to the foundry sand in the sand mixer,
   a step for integrating the quantity of the water supplied to the sand mixer with a digital flow meter, and
   a step for closing a first electromagnetic on-off valve when the integrated water reaches the necessary quantity.

5. The method of claim 4, wherein in the step for closing the first electromagnetic on-off valve, the timing for closing the electromagnetic on-off valve is controlled by a signal transmitted to the electromagnetic on-off valve, which signal is transmitted ahead of time so as to compensate for an amount of water based on the measurement of the amount of water flowing into the sand mixer after closing the electromagnetic on-off valve.

6. The method of claim 4, including a step of closing a second electromagnetic on-off valve connected in parallel with the first electromagnetic on-off valve, and wherein the ratio of the flow rate of the two electromagnetic on-off valves is set between 1:2 and 1:10.

* * * * *